United States Patent [19]

Warriner

[11] Patent Number: Plant 6,665

[45] Date of Patent: Mar. 14, 1989

[54] ROSE PLANT JACREM

[75] Inventor: William A. Warriner, Tustin, Calif.

[73] Assignee: Jackson & Perkins Company, Medford, Oreg.

[21] Appl. No.: 81,435

[22] Filed: Aug. 3, 1987

[51] Int. Cl.[4] ..... A01H 5/00

[52] U.S. Cl. ..... Plt./10

[58] Field of Search ..... Plt./10

*Primary Examiner*—Robert E. Bagwill

*Attorney, Agent, or Firm*—Majestic, Gallagher, Parsons & Siebert

[57] ABSTRACT

A rose variety of the miniature class is provided having bright red flowers, very compact plant habit suitable for four-inch plant production, petiole edge covered with glands, easy propagation as a softwood cutting and bronze-colored new foliage.

1 Drawing Sheet

SUMMARY OF THE INVENTION

The present invention relates to a new and distinct variety of rose plant of the miniature class, which was originated by me by crossing an unnamed seedling with the variety Red Minimo, U.S. Plant Pat. No. 5,770.

The primary objective of this breeding was to produce a new rose variety of the miniature class with clear red flowers, very compact habit and adaptable to production as a four-inch pot plant. This objective was substantially achieved, along with other desirable improvements, as evidenced by the following unique combination of characteristics which are outstanding in the new variety and which distinguish it from its parents as well as from all other varieties of which I am aware. For example, this new rose variety has:

1. Bright red flowers;
2. Very compact plant habit suitable for four-inch pot plant production;
3. Five to seven leaflet leaves;
4. Bronze colored new foliage;
5. Powdery mildew resistance;
6. Petiole edge covered with glands;
7. Propagates readily as a softwood cutting.

Asexual reproduction of this new variety by cuttings, as performed at Irvine, Calif., shows that the foregoing characteristics and distinctions come true to form and are established and transmitted through succeeding propagation.

DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED DESCRIPTION OF THE INVENTION

The following is a detailed description of my new rose cultivar, which has been denominated "Jacrem". Color terminology is in accordance with The Royal Horticultural Society Colour Chart except where an ordinary dictionary significance for the color is apparent.

Observations of the buds and flowers were made from specimens grown in a garden at Irvine, Calif. during June.

Flower

The blooming habit is continuous. The bud size is one-half inch when the petals start to unfurl. The bud form is small, pointed ovoid. The bud color when sepals first divide is near Red Group 44A; when half blown, the upper side of petals is near Red Group 44A and the lower side of petals is near Red Group 44A. The sepals have a color near Green Group 138B. The surface texture is covered with fine hairs. There are three appendaged sepals normally appendaged, and two unappendaged sepals with hairy edge. The receptacle color is near Green Group 138B with a funnel shape, small size and a smooth surface. The peduncle is long, and a smooth surface with very fine hairs. Peduncle color is medium green and the peduncle is stiff, erect and slender.

Bloom

Bloom size is small, with an average open size of one to one and one-fourth inches, borne single and several together, in clusters. When in clusters, the blooms are flat and irregular. The stems are short and strong. The form when first open is cupped to flat. This form then flattens and the outer petals curl back, quill fashion. Under normal conditions there are 25 to 40 petals. The upper side of petals is near Red Group 44A, as is the reverse side of the petals. The base of petals has a very small white to cream colored half moon at the point of attachment to the peduncle with the major color being near Red Group 44A. There are no variegations except for occasional white steaks on petals. The general tonality at the end of the first day shows no change in color. At the end of the third day, the color is still near Red Group 44A.

There is no fragrance. The petal texture is thick, of an oval pointed shape, with the tips being slightly recurved and the edges slightly quilled.

The arrangement is imbricated with few petaloids in the center. The blooms drop off cleanly, and last on the plant for a long period.

Reproductive Parts

The anthers are small and many, of reddish brown color and arranged regularly around the styles and mixed with the petaloids. The filaments are white, the pollen is gold yellow, the styles are greenish white, and the stigmas are greenish white.

Plant

A vigorous upright bush in miniature form that is dwarf and branching.

Foliage

Small size, normal in quantity. The new foliage is reddish green, and the old foliage is green. Normal mid-stem leaves have five to seven leaflets.

The leaflets are of an oval pointed shape, are smooth and glossy, and have a serrated edge. The serration is single. Petiole rachis is reddish, and a smooth underside with prickles. The edge is covered with glands. Stipules are medium and bearded. The foliage is resistant to mildew under normal growing conditions at Irvine, Calif.

Wood

New wood is light green, with a smooth bark. Old wood is green with a smooth bark.

Prickles

There are few prickles on main canes from the base and on laterals from the main canes. The form is medium and straight. Color when young is red.

Small Prickles

There are no small prickles on the main stalks or on the laterals.

Additional Distinguishing Traits

This novel rose plant is highly adapted to production in four-inch pots because of its very compact early flowering growth habit and its ease of propagation as softwood cuttings.

Parentage

The seed parent was an unnamed seedling. The pollen parent was Red Minimo, U.S. Plant Pat. No. 5,770.

Classification

Botanical is rosa hybrid. Commercial is miniature.

I claim:

1. A new and distinct variety of rose plant and parts thereof of the miniature class substantialy as herein shown and described, characterized particularly as to novelty by bright red flowers, ease of propagation by softwood cuttings, very compact plant habit suitable for four-inch pot plantings, bronze-colored new foliage, resistance to powdery mildew, five to seven leaflet leaves and glands on the petiole edge.

* * * * *

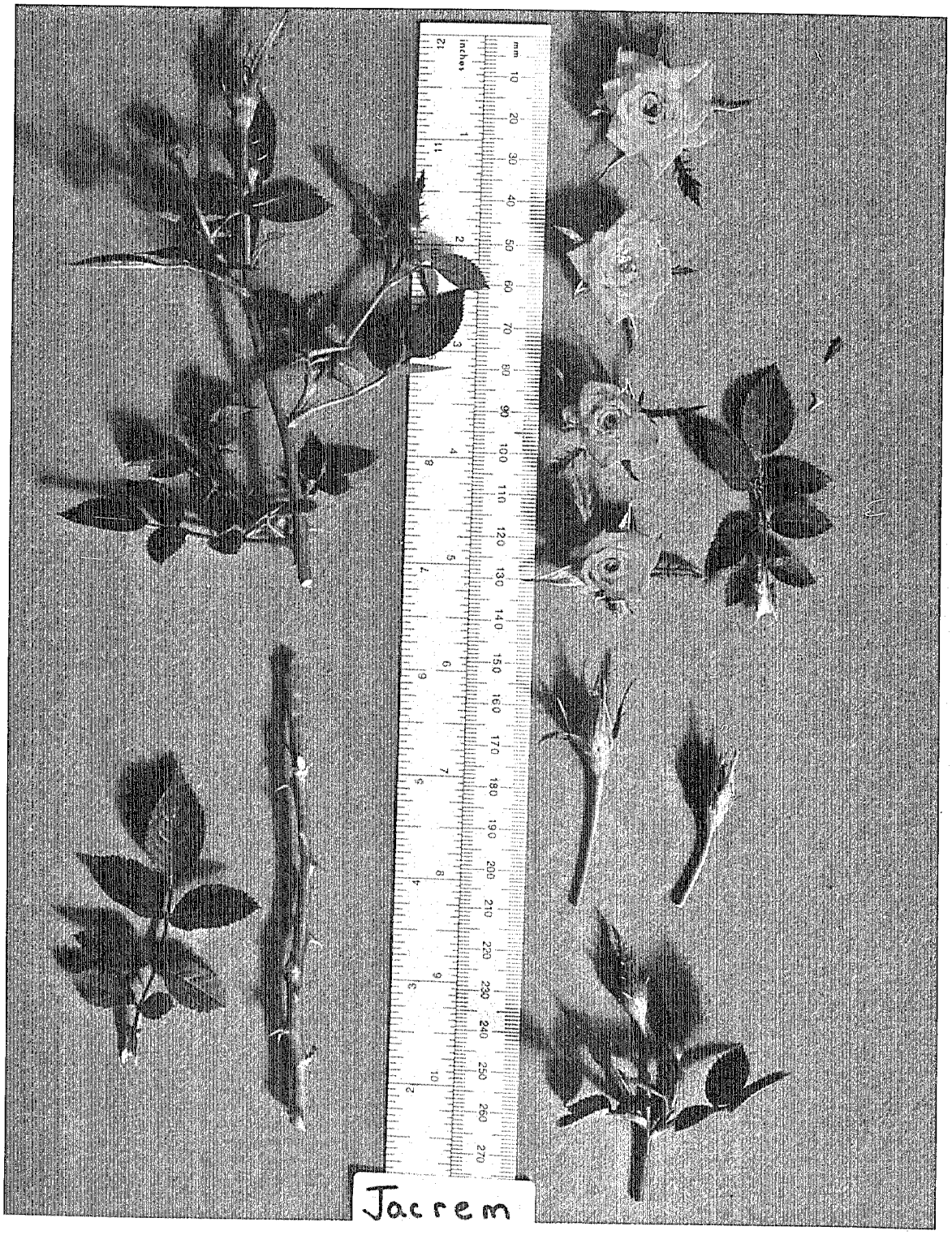
Jacrem